United States Patent [19]

Shindoh et al.

[11] Patent Number: 5,061,589
[45] Date of Patent: Oct. 29, 1991

[54] TONER FOR ELECTROPHOTOGRAPHY

[75] Inventors: Seijin Shindoh, Yono; Michiko Torigoe, Tokyo, both of Japan

[73] Assignee: Nippon Kayaku Kabushiki Kaisha, Tokyo, Japan

[21] Appl. No.: 465,187

[22] PCT Filed: Jun. 22, 1989

[86] PCT No.: PCT/JP89/00622

§ 371 Date: Apr. 3, 1990

§ 102(e) Date: Apr. 3, 1990

[87] PCT Pub. No.: WO89/12849

PCT Pub. Date: Dec. 28, 1989

[30] Foreign Application Priority Data

Jun. 24, 1988 [JP] Japan .................. 63-154605
Jun. 29, 1988 [JP] Japan .................. 63-159378

[51] Int. Cl.$^5$ .................................................. G03G 9/08
[52] U.S. Cl. ......................................... 430/110; 430/115
[58] Field of Search ..................... 430/106.6, 110, 115

[56] References Cited

U.S. PATENT DOCUMENTS 4,737,432  4/1988  Tanaka et al. .................. 430/110
4,886,725  12/1989  Tanaka et al. ................ 430/106.6

FOREIGN PATENT DOCUMENTS 0216295  1/1985  European Pat. Off. .
63-201667  2/1987  Japan .
63-101856  4/1987  Japan .
62-265047  12/1987  Japan .
62-289852  12/1987  Japan .
62-289853  12/1987  Japan .
62-289854  12/1987  Japan .

*Primary Examiner*—John Goodrow
*Attorney, Agent, or Firm*—Nields & Lemack

[57] ABSTRACT

A toner for electrophotography containing a compound represented by the following formula (1)

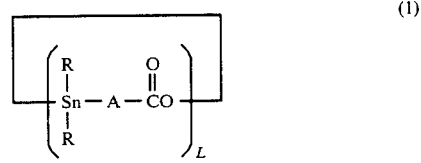

(1)

wherein R represents an alkyl group, —A— represents —O—COCH=CH— or —S—CH$_2$CH$_2$— and L is an integer of 2 to 10.

The toner for electrophotography has a sharp distribution for the charging amount, excellent moisture resistance and stability to aging. As a result, the toner can provide an image of extremely high gradation and shows satisfactory performance of replicate image formation.

9 Claims, No Drawings

TONER FOR ELECTROPHOTOGRAPHY

DESCRIPTION

1. Technical Field

The present invention concerns a toner. More specifically, it relates to a toner for developing electrostatic latent images for electrophotography, electrostatic recording, etc.

2. Background Art

A process for forming an image of electrostatic recording, electrophotography, etc. by utilizing static electricity comprises a step of forming a photoconductive latent image by an optical signal on photosensitive material obtained by coating photoconductive material such as selenium, cadmium sulfide or amorphous silicon on a substrate made of aluminum, paper, etc., and a step of electrically charging colored fine particles of 5-50 μm referred to as a toner frictionally by means carrier (iron powder, ferrite powder, etc.) in two component development or directly in mono component development and then acting them on a photoconductive latent image thereby developing the same.

It is necessary that the toner is applied with electric charge corresponding to the polarity of a photoconductive latent image formed on the photosensitive material, that is, either positive or negative charge.

Generally, fine colored particles referred to as a toner comprises a binder resin and a coloring agent as the essential ingredient and, optionally, a magnetic powder, etc. As a method of applying electric charge to a toner, it is possible to utilize charging property of a binder resin itself without using a charge control agent, but stability to aging and moisture resistance is usually poor and no satisfactory image quality can be obtained by this method. Accordingly, a charge control agent is usually added with an aim of retaining and controlling charges of a toner. The properties required as the quality of a toner includes excellent charging property, flowing property and fixing property, and they are greatly influenced by the charge control agent used for a toner.

As the charge control agent added to a toner, there have been known, (1) colored negative charge control agents such as 2:1 metal complex salt dye (Japanese Patent Publications No. 45-26478 and No. 41-201531) and phthalocyanine pigment (Japanese Patent Application Laid Open (KOKAI) No. 52-45931), and colorless negative charge control agents as described in Japanese Patent Publication No. 59-7384 or Japanese Patent Application Laid Open No. 61-3149, (2) positive charge control agents such as nigrosine dyes, various kinds of quaternary ammonium salts (Journal of Electrostatic Society, 1980, Vol.4, No. 3, P-114). However, a toner containing these charge control agents can not satisfy the property required for the quality of the toner such as charging property and stability to aging. For instance, a toner containing 2:1 metal complex salt dye known as a negative charge control agent has a certain level of charging amount but involves a drawback that the dispersibility of the 2:1 metal complex salt dye to a binder resin is generally poor. Therefore, it does not distribute uniformly in binder resin, and the distribution for the charging amount of the resultant toner remarkably lacks in the sharpness. The resultant image obtained by using such a toner has low gradation and poor image forming performance. In addition, since the 2:1 metal complex salt dye has a hue near black color, it has a drawback that it can be used only for a toner of a restricted hue based on black color. As a nearly colorless negative charge control agent, there can be mentioned a metal complex of an aromatic dicarboxylic acid (Japanese Patent Publication No. 59-7384), but this has a drawback that it can not be completely colorless and dispersibility is not satisfactory. Further, as a colorless negative charge control agent, there has been known a compound proposed by Japanese Patent Application Laid Open (KOKAI) No. 61-3149, but the compound, having a low melting point, involves a drawback that the heat stability upon toner production is poor and production of stable toner is difficult. Accordingly, it has been demanded for the development of a toner in which the charge control agent is well dispersed to a binder resin and uniformly distributed in a toner to provide an image of high gradation.

DISCLOSURE OF INVENTION

The present inventors have made an earnest study for solving the foregoing problems and, as a result, have accomplished the present invention based on the finding that the distribution of the charging amount of the toner is sharp and the charging property is remarkably improved by incorporating the compound of the following formula (1) into a toner.

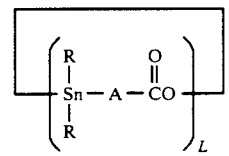

(1)

wherein R represents alkyl group, —A— represents —O—COCH=CH— or —S—CH$_2$CH$_2$— and L is an integer of 2 to 10.

The compound of the formula (1) functions as a negative charge control agent which has a satisfactory compatibility with a binder resin and a toner incorporated with the compound shows high specific charging amount and satisfactory stability to aging and, accordingly, can provide stable and clear image upon forming an image in electrostatic recording even if a toner is stored on a long period of time.

As preferred examples of the compound of the formula (1) incorporated as a charge control agent into a toner in the present invention there can be mentioned the following compounds:

Specific examples of compound

As the compounds represented by the following formula (2):

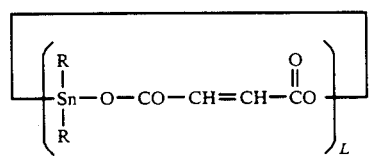

(2)

wherein R and L have the same meanings as described above, there can be mentioned the followings.

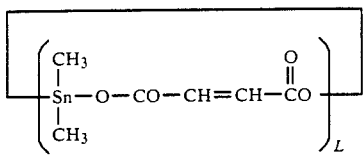

(3)

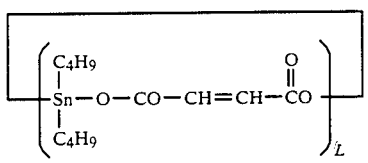

(4)

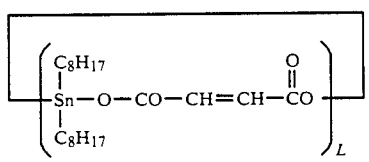

(5)

Each of the compounds (3), (4) and (5) is a mixture of compounds in which L is 2 to 10.

These compounds can be synthesized by a known methods, for example, by acting maleic acid to an organic tin oxide. Further, a compound belonging to the following formula (6) can also be mentioned as a preferred example.

$$\left( \begin{array}{c} R \\ | \\ -Sn-S-CH_2CH_2CO- \\ | \\ R \end{array} \right)_L$$

(6)

wherein R and L have the same meanings as described above.

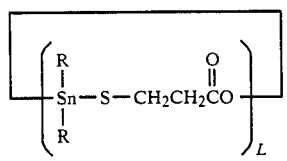

(7)

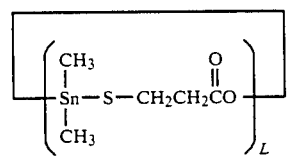

(8)

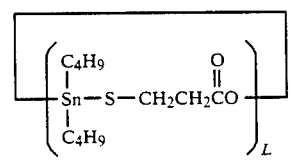

(9)

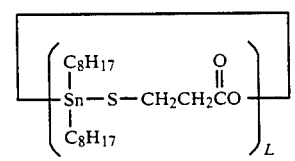

Each of the compounds (7), (8) and (9) is a mixture of compounds in which L is 2 to 10. These compounds can be synthesized by known methods, for example, by acting a corresponding carboxylic acid, maleic acid anhydride and a corresponding alcohol to an organic tin sulfide.

BEST MODE FOR CARRYING OUT THE INVENTION

For producing a toner containing the compound of the formula (1) described above, there is a method of kneading a mixture comprising the compound of the formula (1), a coloring agent and a binder resin in a device capable of mixing under heating such as a heating kneader or twin roll, under the molten state of the binder resin, which is then cooled to solidify and pulverized by a pulverizer such as a jet mill or ball mill into 1 to 30 μm (particle size), or a method of dissolving a coloring agent, a binder resin and the compound of the formula (1) together into a solvent (for example, acetone or ethylacetate), applying agitation, then pouring into water for reprecipitation, filtering, drying and then pulverizing by a pulverizer such as a ball mill into 1 to 30 μm (particle size).

The binder resin is used usually by 8.9 to 65%, more preferably, 98 to 85%, the coloring agent is used by 1.0 to 15%, more preferably, 1.5 to 10% and the charge control agent is used by 0.1 to 30%, more preferably, 0.5 to 5% (each in weight ratio) in this case.

The coloring agent for use with the toner for electrophotograph according to the present invention (abbreviations shown hereinafter represent the following meanings: CI: Color Index, Pig: Pigment, Dis: disperse, Sol: solvent, Y: yellow, R: red and B: blue) can include those known coloring agents such as inorganic pigment, for example, carbon black and ultramarine; organic pigments, for example, CI-Pig-Y-1, CI-Pig-R-9, CI-Pig-B15, etc.; oil soluble dyes such as CI-Sol-Y-93, CI-Sol-R-146, CI-Sol-B-35, CI-Dis-Y-42, CI-Dis-R-59, CI-Sol-B-81, etc. As the binder resin, these can be used polystyrene, styrene-acrylic acid copolymer, styrene propylene copolymer, styrene acrylonitrile copolymer, acryl resin, styrene-maleic acid copolymer, polyvinyl chloride, polyvinyl acetate, olefin resin, polyester resin, polyurethane resin and epoxy resin, either along or a mixture.

In addition, into the toner for electrophotography according to the present invention, there may be added, as required, a flowing agent such as silicon oxide, anti-foggant such as mineral oil, various kinds of magnetic substance used for monocomponent development, electrifying agent such as zinc oxide, anti set agent such as low molecular weight polyethylene and low molecular weight polypropylene.

The toner obtained in the present invention is formulated into a developer, for example, by mixing with an iron powder (carrier) of about 200 mesh at a weight ratio, for example, of 2 to 8: 98 to 92 (toner: iron powder) and used for the developing step in electrophotography.

The toner for electrophotography according to the present invention has sharp charging amount distribution and satisfactory stability to aging as compared with toners using conventional charge control agent. As a result, it has a feature capable of obtaining an image of extremely high gradation, while showing excellent performance of replicate image formation.

EXAMPLE

The present invention is to be explained more specifically by way of examples. In the examples, "parts" means "parts by weight" unless otherwise specified.

Example 1

| | |
|---|---|
| Styrene-butyl acrylate copolymer (binder) | 100 parts |
| Low molecular weight polyethylene | 2 parts |
| CI-Dis-Y-164 (coloring agent) | 1.2 parts |
| Compound of Formula (3) (mixture of L = 2-10) | 1.5 parts |

The above mentioned composition was melt kneaded by a kneader adjusted to 140° C. for 10 min and then cooled to solidify. Then, after coarsely pulverizing by a coarse pulverizer, it was finely pulverized by a jet mill pulverizer and then classified in an air stream classifier to obtain a toner of 8 to 20 μm particle size.

The resultant toner was mixed with iron powder carrier of about 200 mesh at a weight ratio of 3:97 (toner:iron powder carrier) to obtain a developer A. Then, when the initial specific charging amount of the developer A was measured by a blow off charge amount measuring device, it was $-23.4$ μc/g. When copying was conducted in a copying machine using the developer A, a clear yellow image excellent in gradation and not deteriorating the hue inherent to the coloring agent was obtained. Further, when a test for stability to aging was conducted by using the developer A (test for the change of the charging amount with time and test for moisture resistance and stability to aging), the results shown in the following Table 1 were obtained.

TABLE 1

| | Test for change of charging amount with time ($-\mu c/g$) (hour) | | | | | | Test for moisture resistance with time ($-\mu c/g$) | | |
|---|---|---|---|---|---|---|---|---|---|
| | 1 | 2 | 3 | 4 | 5 | 6 | Initial | After 1 week | Decreasing rate (%) |
| Developer A | 23.6 | 23.8 | 23.5 | 23.3 | 23.1 | 23.0 | 23.4 | 23.1 | 1.3 |

As can be seen from the results above, the stability of the developer A to aging was excellent.

Stability test to aging

Test for the change of charging amount with time

The developer A (mixture of toner and iron power carrier) was weighed in a plastic vessel, applied with ball milling at 100 rpm, to measure the charging amount of the toner on every hours (1 to 6 hr).

Test for moisture resistance with time

After charging for one hour in a plastic vessel according to the above mentioned method "test for the change of charging amount with time", the developer was left for one week in an 10% moisture atmosphere (at room temperature) with the vessel open to measure the charging amount of the toner.

EXAMPLE 2

A developer B was obtained in the same procedures as in Example 1 except for using 2.0 parts of the compound of the formula (7) (mixture of L = 2 to 10) instead of the compound of the formula (3) in Example 1. The initial specific charging amount of the developer B was $-21.4$ μc/g. When the stability test to aging was conducted, the results were obtained as shown in the following Table 2.

TABLE 2

| | Test for change of charging amount with time ($-\mu c/g$) (hour) | | | | | | Test for moisture resistance with time ($-\mu c/g$) | | |
|---|---|---|---|---|---|---|---|---|---|
| | h: hour | | | | | | | After | Decreasing |
| | 1 h | 2 h | 3 h | 4 h | 5 h | 6 h | Initial | 1 week | rate (%) |
| Developer B | 21.6 | 21.8 | 21.5 | 21.3 | 21.1 | 21.0 | 21.4 | 21.1 | 1.4 |

As apparent from the foregoing results, the stability of the developer B to aging was excellent.

EXAMPLE 3

| | |
|---|---|
| Polyester resin (binder) | 100 parts |
| Carbon black (coloring agent) | 6.0 parts |
| Compound of formula (4) (mixture of L = 2 to 10) | 2.0 parts |

The mixture of the above mentioned composition was melt kneaded by a kneader adjusted to 160° C. for 10 min and then cooled to solidify. Then, after coarsely pulverizing by a coarse pulverizer, it was finely pulverized by a jet mill pulverizer and then classified in an air stream classifier to obtain a toner of 8 to 20 μm particle size.

The resultant toner was mixed with an iron powder carrier of about 200 mesh at a weight ratio of 3:97 (toner:iron powder carrier) to obtain a developer C. Then, when the initial specific charging amount of the developer C was measured by a blow off charge amount measuring device, it was $-21.3$ μc/g. When copying was conducted in a copying machine using the developer C, a clear black image of excellent gradation was obtained.

When the same stability test to aging as in Example 1 was conducted by using the developer C, the results as shown in the following Table 3 were obtained.

TABLE 3

|  | Test for change of charging amount with time ($-\mu c/g$) (hour) | | | | | | Test for moisture resistance with time ($-\mu c/g$) | | |
| --- | --- | --- | --- | --- | --- | --- | --- | --- | --- |
|  | h: hour | | | | | | | After | Decreasing |
|  | 1 h | 2 h | 3 h | 4 h | 5 h | 6 h | Initial | 1 week | rate (%) |
| Developer C | 21.5 | 21.6 | 21.4 | 21.3 | 21.2 | 21.0 | 21.6 | 21.3 | 1.4 |

As apparent from the results, the stability of the developer C to aging was excellent.

EXAMPLE 4

A developer D was obtained in the same procedures as in Example 3 except for using 1.5 parts of the compound of the formula (8) (mixture of L = 2 to 10) instead of the compound of the formula (4) in Example 3. The initial specific charging amount of the developer D was $-19.8$ $\mu c/g$. When the stability test to aging was conducted, the results as shown in the following Table 4 were obtained.

TABLE 4

|  | Test for change of charging amount with time ($-\mu c/g$) (hour) | | | | | | Test for moisture resistance with time ($-\mu c/g$) | | |
| --- | --- | --- | --- | --- | --- | --- | --- | --- | --- |
|  | h: hour | | | | | | | After | Decreasing |
|  | 1 h | 2 h | 3 h | 4 h | 5 h | 6 h | Initial | 1 week | rate (%) |
| Developer D | 19.7 | 19.9 | 19.7 | 19.5 | 19.4 | 19.2 | 19.6 | 19.3 | 1.5 |

As apparent from the foregoing results, the stability of the developer D to aging was excellent.

EXAMPLE 5

| Styrene-methyl acrylate copolymer (binder) | 100 parts |
| --- | --- |
| Low molecular weight polypropylene | 3 parts |
| CI Sol-Blue-111 (coloring agent) | 1.5 parts |
| Compound of formula (5) (mixture of L = 2 to 10) | 2.5 parts |

The mixture described above was dissolved into 1000 parts of a mixed solvent of acetone and ethyl acetate (1:1.volume ratio) and then stirred at ordinary temperature for 1 hour. Then, the mixed solution was dropped into 10000 parts of water under stirring to reprecipitate. By filtering and drying the resultant crystals, toner of coarse particles were obtained. Then, they were finely pulverized by a jet mill pulverizer and, further, classified by an air stream classifier to obtain toners of 8 to 20 $\mu$m particle size.

The resultant toner was mixed with an iron powder carrier of about 200 mesh at a weight ratio of 3:97 (toner:iron powder carrier) to obtain a developer E. Then, when the initial specific charging amount of the developer E was measured by a blow off charge amount measuring device, it was $-23.3$ $\mu c/g$. When copying was conducted in a copying machine using the developer E, a clear blue image of excellent gradation and not deteriorating the hue inherent to the coloring agent was obtained.

When the same stability test to aging as in Example 1 was conducted by using the developer E, the results as shown in the following Table 5 were obtained.

TABLE 5

|  | Test for change of charging amount with time ($-\mu c/g$) (hour) | | | | | | Test for moisture resistance with time ($-\mu c/g$) | | |
| --- | --- | --- | --- | --- | --- | --- | --- | --- | --- |
|  | h: hour | | | | | | | After | Decreasing |
|  | 1 h | 2 h | 3 h | 4 h | 5 h | 6 h | Initial | 1 week | rate (%) |
| Developer E | 23.2 | 23.4 | 23.1 | 22.9 | 22.7 | 22.6 | 23.1 | 22.7 | 1.7 |

As shown in the results above, the stability of the developer E to aging was excellent.

EXAMPLE 6

A developer F was obtained in the same procedures as in Example 5 except for using 1.5 parts of the compound of the formula (9) (mixture of L=2 to 10) instead of the compound of the formula (5) in Example 5. The initial specific charging amount of the developer F was $-22.1$ $\mu c/g$. When the stability test to aging was conducted, the results as shown in the following Table 6 were obtained.

TABLE 6

|  | Test for change of charging amount with time ($-\mu c/g$) (hour) | | | | | | Test for moisture resistance with time ($-\mu c/g$) | | |
| --- | --- | --- | --- | --- | --- | --- | --- | --- | --- |
|  | h: hour | | | | | | | After | Decreasing |
|  | 1 h | 2 h | 3 h | 4 h | 5 h | 6 h | Initial | 1 week | rate (%) |
| Developer F | 22.2 | 22.4 | 22.1 | 21.7 | 21.4 | 21.3 | 22.1 | 21.7 | 1.8 |

As apparent from the results above, the stability of the developer F to aging was excellent.

INDUSTRIAL APPLICABILITY

The toner for electrophotography obtained in the present invention has sharp charge amount distribution excellent moisture resistance and stability to aging. As a result, the toner can provide an image of high gradation and show satisfactory performance of replicate image formation. Further, since the charge control agent itself used in the toner according to the present invention is substantially colorless, it is possible to select to coloring agent in line with the hue required for the color toner and the hue inherent to the dye or pigment is not deteriorated at all and, accordingly,, it has excellent industrial applicability as the toner in electrophotography and electrostatic recording.

We claim:

1. A toner for electrophotography containing a compound represented by the following formula (1)

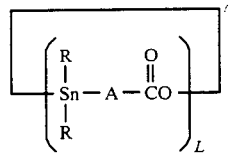

wherein R represents an alkyl group, —A— represents —O—COCH=CH— or —S—CH$_2$CH$_2$— and L is an integer of 2 to 10.

2. A toner for electrophotography according to claim 1, wherein the compound represented by the formula (1) is a compound represented by the following formula:

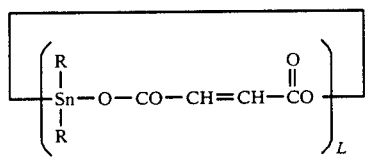

wherein R and L in the formula (2) have the same meanings as described above.

3. A toner for electrophotography according to claim 2, wherein the compound represented by the formula (2) is a compound represented by the following formula:

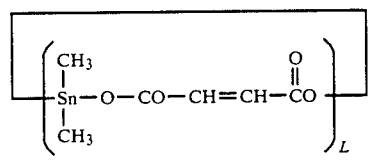

wherein L in the formula (3) has the same meanings as described above.

4. A toner for electrophotography according to claim 2, wherein the compound represented by the formula (2) is a compound represented by the following formula:

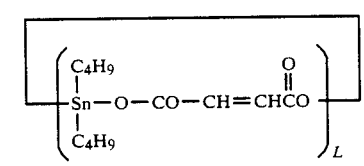

wherein L in the formula (4) has the same meanings as described above.

5. A toner for electrophotography according to claim 2, wherein the compound represented by the formula (2) is a compound represented by the following formula:

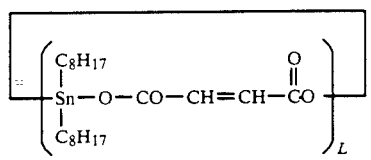

wherein L in the formula (5) has the same meanings as described above.

6. A toner for electrophotography according to claim 1, wherein the compound represented by the formula (1) is a compound represented by the following formula:

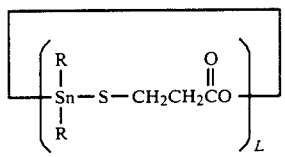

wherein R and L in the formula (6) have the same meanings as described above.

7. A toner for electrophotography according to claim 6, wherein the compound represented by the formula (6) is a compound represented by the following formula:

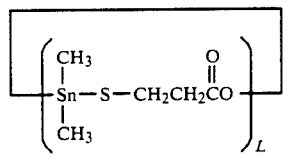

wherein L in the formula (7) has the same meanings as described above.

8. A toner for electrophotography according to claim 6, wherein the compound represented by the formula (6) is a compound represented by the following formula:

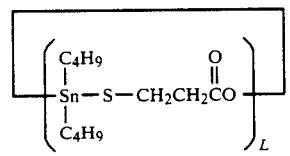

wherein L in the formula (8) has the same meanings as described above.

9. A toner for electrophotography according to claim 6, wherein the compound represented by the formula (6) is a compound represented by the following formula:

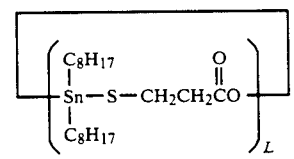

wherein L in the formula (9) has the same meanings as described above.

* * * * *